United States Patent
Imperante

(10) Patent No.: US 6,756,034 B1
(45) Date of Patent: Jun. 29, 2004

(54) POLYPHOSPHATED SILICONE POLYMERS IN PERSONAL CARE APPLICATIONS

(75) Inventor: John Imperante, Somerville, NJ (US)

(73) Assignee: Phoenix Chemical Inc., Somerville, NJ (US)

( * ) Notice: Subject to any disclaimer, the term of this patent is extended or adjusted under 35 U.S.C. 154(b) by 264 days.

(21) Appl. No.: 10/134,089

(22) Filed: Apr. 29, 2002

(51) Int. Cl.⁷ ............................................. A61K 7/075
(52) U.S. Cl. ................................... 424/70.12; 424/70.1
(58) Field of Search ............................. 424/70.1, 70.12

(56) References Cited

U.S. PATENT DOCUMENTS 5,382,381 A * 1/1995 Imperante et al. ............ 516/55

* cited by examiner

Primary Examiner—Jyothsna Venkat

(57) ABSTRACT

The invention is directed toward a process for conditioning hair and skin, using a silicone polyphosphate that has between 6 and 20 phosphate groups in the molecule. The compounds having multi-phosphate groups have been found to be surprisingly effective conditioners when compared to compounds having fewer or no phosphate groups present.

13 Claims, No Drawings

POLYPHOSPHATED SILICONE POLYMERS IN PERSONAL CARE APPLICATIONS

BACKGROUND OF THE INVENTION

1. Field of Invention

The present invention relates to a process for using specific silicone phosphate esters in personal care applications, where the proper selection of the phosphate ester allows for (a) maximum foam, (b) minimum irritation and (c) optimum skin feel. The process relies upon the selection of a specific type of silicone phosphate ester. The proper phosphate ester: (a) is a mono-esters made by phosphation with polyphosphoric acid, (b) contains between 45 and 60% polyoxyethylene in the molecule by weight, (c) has between 6 and 15 phosphate groups, and (d) has free hydroxyl groups present in the molecule.

When this combination of structural attributes are preset, an aqueous cosmetic formulation can be made which is (a) clear, (b) high foaming and (c) conditioning to the skin and hair, without building up.

2. Object of the Invention

It is the object of the present invention to provide a process for using specific silicone phosphate esters in personal care applications, where the proper selection of the phosphate ester allows for (a) maximum foam, (b) minimum irritation and (c) optimum skin feel. The process relies upon the selection of a specific type of silicone phosphate ester. The proper phosphate ester: (a) is a mono-esters made by phosphation with polyphosphoric acid, (b) contains between 45 and 60% polyoxyethylene in the molecule by weight, (c) has between 6 and 15 phosphate groups, and (d) has free hydroxyl groups present in the molecule.

3. Description of the Arts and Practices

Silicone oils (polydimethylsiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high-pressure equipment, surface-active agents and generally results in a milky emulsion. Emulsions have experienced stability problems both in terms of freeze thaw instability and upon heating. This has resulted in minimal acceptance of them in commercial products.

U.S. Pat. No. 5,070,171 issued Dec. 3, 1991 to O'Lenick, incorporated herein by reference, describes a variety of silicone phosphate esters. These products are described as being useful in a variety of applications, from fiber and textile lubricants, to alkali stable products. We have surprisingly learned that the compounds of the O'Lenick invention can be modified to produce products with the desired properties for personal care applications where aqueous products that are (a) clear, (b) high foaming and (c) conditioning to the skin and hair, without building up are achieved.

U.S. Pat. No. 5,859,161 to Imperante et al issue Jan. 12, 1999, teaches that phosphate esters can be used to migrate irritation in sulfated surfactants.

None of these patents suggest that by selecting the proper silicone phosphate, a clear, high foaming, highly conditioning solvent free aqueous product could be prepared.

THE INVENTION

SUMMARY OF THE INVENTION

The present invention relates to a to a process for using specific silicone phosphate esters in personal care applications, where the proper selection of the phosphate ester allows for (a) maximum foam, (b) minimum irritation and (c) optimum skin feel.

DESCRIPTION OF THE INVENTION

The process comprises contacting the hair or skin with an effective conditioning concentration of a silicone phosphate conforming to the following structure:

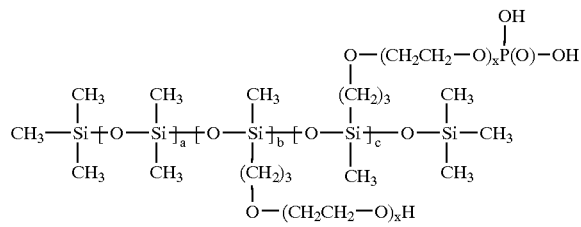

a is an integer ranging from 1 to 50;

b is an integer ranging from 0 to 20, c is an integer ranging from 6 to 20;

with the proviso that (a) times (0.2)+1<b+c x is an integer ranging from 8 to 20.

The products of the present invention are prepared by reaction of a hydroxyl containing silicone polymer with a suitable phosphating reagent.

Specific silicone compounds useful as raw materials in the preparation of the compounds of the present invention are available from Siltech LLC, Dacula Ga. The trade name is given merely for illustration, the structures were elucidated and are necessary for the practice of the process of the current invention.

PREFERRED EMBODIMENT

In a preferred embodiment a is an integer ranging from 2 to 10.

In another preferred embodiment b is an integer ranging from 10 to 15.

In another preferred embodiment a is an integer ranging from 2 to 10 and b is an integer ranging from 10 to 15.

In another preferred embodiment x is an integer ranging from 9 to 12, and a is an integer ranging from 2 to 10.

In another preferred embodiment b is an integer ranging from 10 to 15 and x is an integer ranging from 9 to 12.

In another preferred embodiment a is 10, b is 5, c is 12 and x is 10.

In another preferred embodiment a is 10, b is 5, c is 12 and x is 10.

In another preferred embodiment a is 5, b is 2, c is 12 and x is 10.

In another preferred embodiment x is 12.

In another preferred embodiment b is 10.

In another preferred embodiment a is 11.

In another preferred embodiment b is 5.

EXAMPLES

Phosphation

Phosphating Agents

Polyphosphoric Acid (PPA) is 115% phosphoric acid. When used as a phosphating agent it gives more monoester than the phosphorus pentoxide.

Phosphorus pentoxide is $P_2O_5$. It is more aggressive in phosphation and results in more diester and for this reason is simply not of interest in the practice of the present invention.

The silicone phosphates of this invention can be prepared by reacting the hydroxyl containing silicone polymer with polyphosphoric acid under mild conditions.

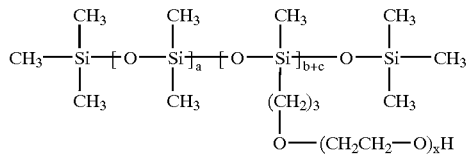

+ c moles of polyphosphoric acid →

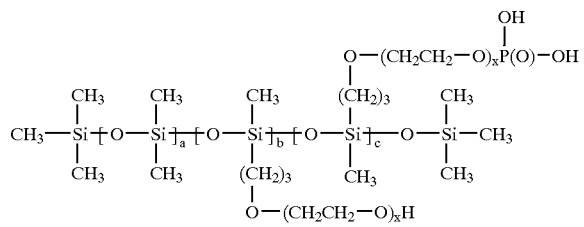

a is an integer ranging from 1 to 50;

b is an integer ranging from 0 to 20, c is an integer ranging from 6 to 20;

with the proviso that (a) times (0.2)+1 is less than b+c x is an integer ranging from 8 to 20.

The following examples further illustrate the objects and advantages of this invention, though it should be understood that the various reactants and amounts thereof, reaction conditions, and other details are merely illustrative and should not be construed to unduly limit this invention.

Examples

Silicone Glycols

Silicone glycols suitable as raw materials in the preparation of the compounds of the present invention are commercially available from Siltech LLC Dacula, Ga. They conform to the following structure:

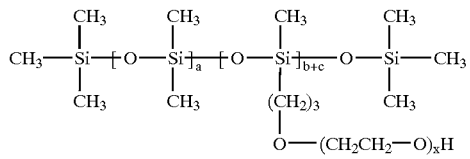

Examples 1–10

| Example | a | b | c | x |
|---|---|---|---|---|
| 1 | 10 | 4 | 6 | 10 |
| 2 | 1 | 1 | 8 | 8 |
| 3 | 20 | 10 | 10 | 12 |
| 4 | 50 | 5 | 20 | 10 |
| 5 | 10 | 2 | 12 | 20 |
| 6 | 20 | 10 | 15 | 10 |
| 7 | 5 | 8 | 10 | 12 |
| 8 | 10 | 10 | 8 | 8 |
| 9 | 8 | 20 | 12 | 10 |
| 10 | 6 | 5 | 9 | 10 |

Examples for Comparison

Not of the Process of the Present Invention

| Example | a | b | c | x |
|---|---|---|---|---|
| 11 | 20 | 1 | 2 | 4 |
| 12 | 2 | 2 | 2 | 8 |
| 13 | 0 | 0 | 1 | 6 |
| 14 | 5 | 0 | 1 | 10 |

GENERAL PROCEDURE

The specified amount of hydroxy silicone compound (Examples 1–10) is added to a suitable reaction vessel. Next add 100.0 grams of polyphosphoric acid is charged to under good agitation over a 2 hr. period. The exothermic reaction raises the temperature of the mixture to about 70 C. After 1 hour slowly raise the temperature to 100 C. and hold 2–4 hours.

| | Silicone Glycol | |
|---|---|---|
| Example | Example | Grams |
| 15 | 1 | 1079.0 |
| 16 | 2 | 577.0 |
| 17 | 3 | 1454.0 |
| 18 | 4 | 889.0 |
| 19 | 5 | 1239.0 |
| 20 | 6 | 1038.0 |
| 21 | 7 | 1214.0 |
| 22 | 8 | 1168.0 |
| 23 | 9 | 1548.0 |
| 24 | 10 | 934.0 |
| 25 | 11 | 2523.0 |
| 26 | 12 | 1094.0 |
| 27 | 13 | 545.0 |
| 28 | 14 | 1091.0 |

Application Evaluation

The compounds of the present invention are all clear, slightly yellow liquids, which are very well suited for use in personal care applications. While not wanting to be held to one explanation, the presence of the polyphosphate group on these molecules provides a different micelle in aqueous solution. A poly-anionic large micelle forms that provides liquid crystals. These liquid crystals make the product have the desired skin feel and hair conditioning.

Examples 15–23 are the compounds of the present invention. They are water soluble, giving clear solutions. They have outstanding conditioning properties when applied to hair and skin. They provide a surprisingly high level of foam. These properties make the above compounds very desirable in the formulation of personal care products including shampoos, bubble baths, body wash, and after-shave products.

Examples for Comparison

Not of the Process of the Present Invention

| Example | a | b | c | x | |
|---------|----|----|----|----|---|
| 24 | 20 | 2 | 1 | 4 | water insoluble |
| 25 | 2 | 2 | 2 | 8 | poor conditioning |
| 26 | 0 | 1 | 0 | 6 | irritating to eye/ poor conditioning |
| 27 | 5 | 1 | 0 | 10 | water insoluble |

Examples 24–27 are the compounds that are not the topic of the present invention. They lack one or more of the desired properties of the compounds of the present invention and consequently are not useful in making high foaming, water soluble, clear products that give outstanding skin feel. They are not poly anionic materials having 6–20 anionic groups and consequently do not form liquid crystals.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A process for conditioning hair which comprises contacting the hair with an effective conditioning concentration of a silicone phosphate conforming to the following structure:

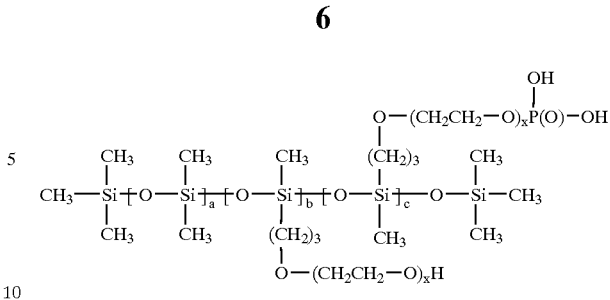

a is an integer ranging from 1 to 50;
b is an integer ranging from 0 to 20,
c is an integer ranging from 6 to 20;
with the proviso that (a) times (0.2)+1 is less than b+c;
x is an integer ranging from 8 to 20.

2. A process of claim 1 wherein a is an integer ranging from 2 to 10.

3. A process of claim 1 wherein b is an integer ranging from 10 to 15.

4. A process of claim 2 wherein b is an integer ranging from 10 to 15.

5. A process of claim 1 wherein x is an integer ranging from 9 to 12.

6. A process of claim 2 wherein x is an integer ranging from 9 to 12.

7. A process of claim 3 wherein x is an integer ranging from 9 to 12.

8. A process of claim 1 wherein a is 10, b is 5, c is 12 and x is 10.

9. A process of claim 1 wherein a is 5, b is 2, c is 12 and x is 10.

10. A process of claim 1 wherein x is 12.

11. A process of claim 1 wherein b is 10.

12. A process of claim 1 wherein a is 11.

13. A process of claim 1 wherein b is 5.

* * * * *